US00PP35565P2

(12) United States Plant Patent
Bailey

(10) Patent No.: US PP35,565 P2
(45) Date of Patent: Dec. 26, 2023

(54) ***HEUCHERA* PLANT NAMED 'MS2020'**

(50) Latin Name: *Heuchera villosa*
Varietal Denomination: MS2020

(71) Applicant: Matthew Bailey, Ankeny, IA (US)

(72) Inventor: Matthew Bailey, Ankeny, IA (US)

(73) Assignee: RIJNBEEK AND SON PERENNIALS EXPORT B.V., Boskoop (NL)

( * ) Notice: Subject to any disclaimer, the term of this patent is extended or adjusted under 35 U.S.C. 154(b) by 0 days.

(21) Appl. No.: 18/115,853

(22) Filed: Mar. 1, 2023

(30) Foreign Application Priority Data

May 18, 2022 (QZ) ..... PBR 20221250

(51) Int. Cl.
*A01H 5/12* (2018.01)
*A01H 6/80* (2018.01)

(52) U.S. Cl.
USPC ..... Plt./440

(58) Field of Classification Search
USPC ..... Plt./440
CPC ... A01H 5/12; A01H 5/02; A01H 5/00; A01H 6/80
See application file for complete search history.

(56) References Cited

U.S. PATENT DOCUMENTS

PP15,945 P2 * 9/2005 Egger ..... A01H 6/80 Plt./440

* cited by examiner

*Primary Examiner* — June Hwu
(74) *Attorney, Agent, or Firm* — Penny J Aguirre

(57) ABSTRACT

A new cultivar of *Heuchera* plant named 'MS2020' that is characterized by its young foliage that is bronze in color and mature foliage that is bronzy green-yellow in color with veins that are similar in color to the leaf lamina, its good winter hardiness with hardiness at least to U.S.D.A. Zone 4, and its strong garden performance.

3 Drawing Sheets

Botanical classification: *Heuchera villosa.*
Cultivar designation: 'MS2020'.

CROSS REFERENCE TO A RELATED APPLICATION

This application claims priority to European Community Plant Variety Office (CPVO) Plant Breeder's Rights Application No. No. 2022/1250, filed May 18, 2022. The Applicant received the information for the Plant breeders' rights application directly from the Inventor.

BACKGROUND OF THE INVENTION

The present invention relates to a new and distinct cultivar of *Heuchera villosa*, botanically known as *Heuchera villosa* 'MS2020' and is hereinafter referred to by its cultivar name 'MS2020'.

The new cultivar arose from an ongoing breeding program conducted by the Inventor in Ankeny, Iowa. The goal of the breeding program is to develop new cultivars of *Heuchera* with unique foliage coloration with improved growing and garden qualities. The new cultivar resulted from a cross made between unnamed and unpatented proprietary plants from the Inventor's breeding program as both the female and male parents in 2011. 'MS202' was selected as a single unique plant in summer of 2012 from the resulting seedlings.

Asexual propagation of the new cultivar was first accomplished under the direction of the Inventor by division in 2012 in Ankeny, Iowa. Asexual propagation of the new cultivar by division and tissue culture using meristematic tissue has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'MS2020' as a new and unique cultivar of *Heuchera.*

1. 'MS2020' exhibits young foliage that is bronze in color and mature foliage that is bronzy green-yellow in color with veins that are similar in color to the leaf lamina.
2. 'MS2020' exhibits good winter hardiness with hardiness at least to U.S.D.A. Zone 4.
3. 'MS2020' exhibits strong garden performance.

The seed parent of 'MS2020' differs from 'MS2020' in having leaves that are green in color. The pollen parent of 'MS2020' differs from 'MS2020' in having leaves that are green in color and have a glossier surface. 'MS2020' can be most closely compared to the *Heuchera* cultivars 'Peach Flambe' (U.S. Plant Pat. No. 17,195) and 'Marmalade' (U.S. Plant Pat. No. 15,945). 'Peach Flambe' is similar to 'MS2020' in flower color. 'Peach Flambe' differs from 'MS2020' in having young foliage that is orange-red in color, mature foliage that is bronzy orange in color, leaf veins that differ in color from the leaf lamina, in being less winter hardy, and poorer performance in the garden. 'Marmalade' is similar to 'MS2020' in foliage color. 'Marmalade' differs from 'MS2020' in having leaves with deeper lobes with margins that are more undulated, in being less winter hardy, and poorer performance in the garden.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales that fall within a one-year grace period prior to the filing date. Disclosure of first sale date on the CPVO plant breeder's application refers to distribution of trial plants only. Disclosures include website listing by isu-perennials, Rijnbeek en Zoon, KVBC, Groen-Direkt, Kwekerij, and Pod Oslonami.

BRIEF DESCRIPTION OF THE DRAWINGS

The accompanying color photographs illustrate the overall appearance and distinct characteristics of the new *Heuchera*. The photographs were taken of a plant 8 months in age of the new cultivar as grown outdoors in a 17-cm container in Boskoop, The Netherlands.

The photograph in FIG. 1 provides a side view of the plant of 'MS2020' in bloom.

Figure 1:
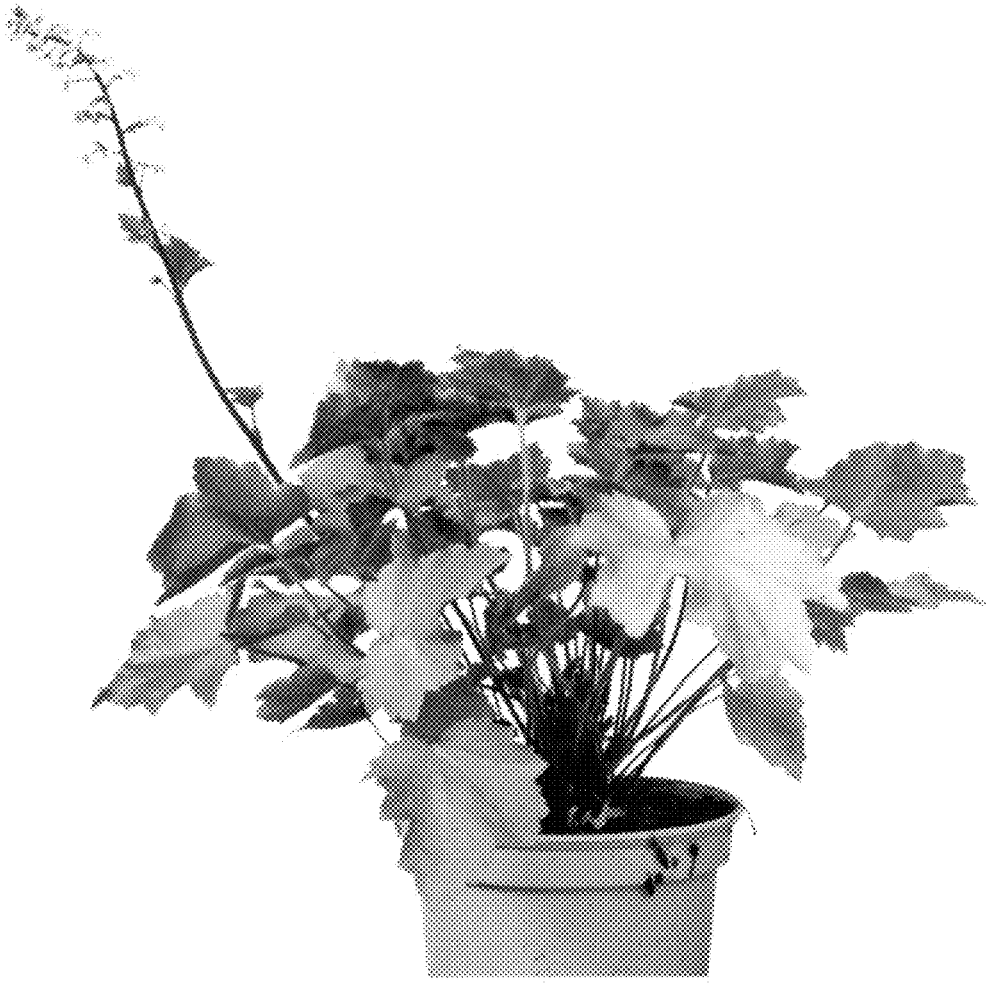
Figure 2:
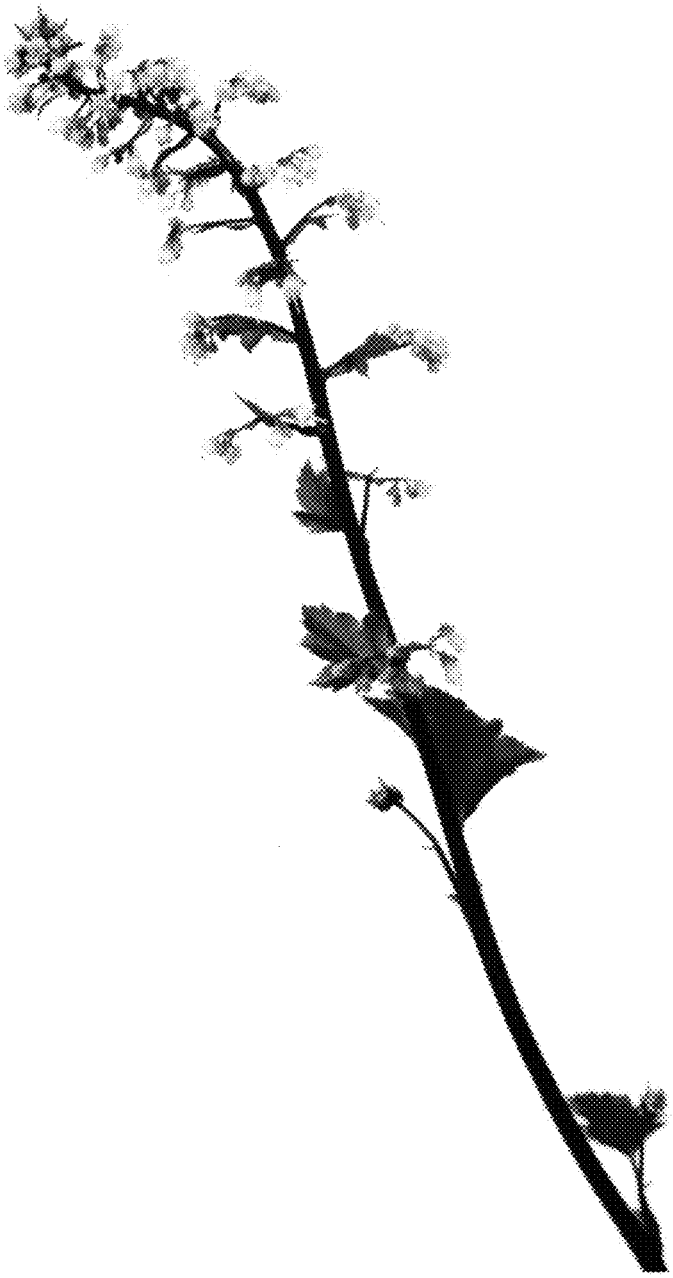

The photograph in FIG. 2 provides a close up of an inflorescence of 'MS2020'.

Figure 3:
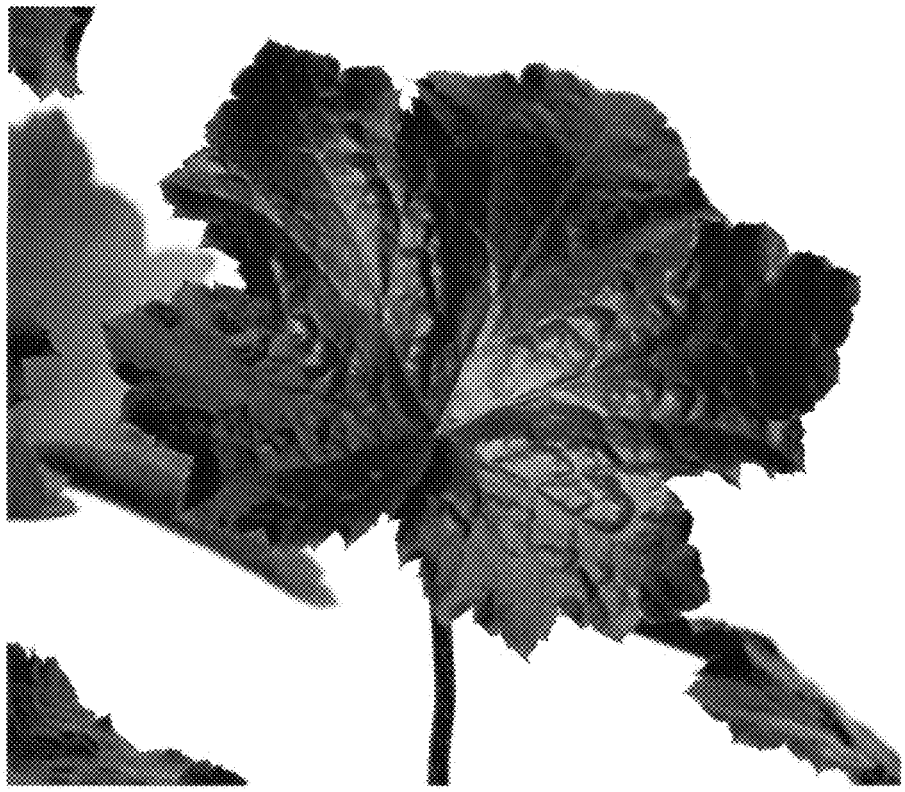

The photograph in FIG. 3 provides a close-up view of the young foliage colors of 'MS2020'.

Figure 4:
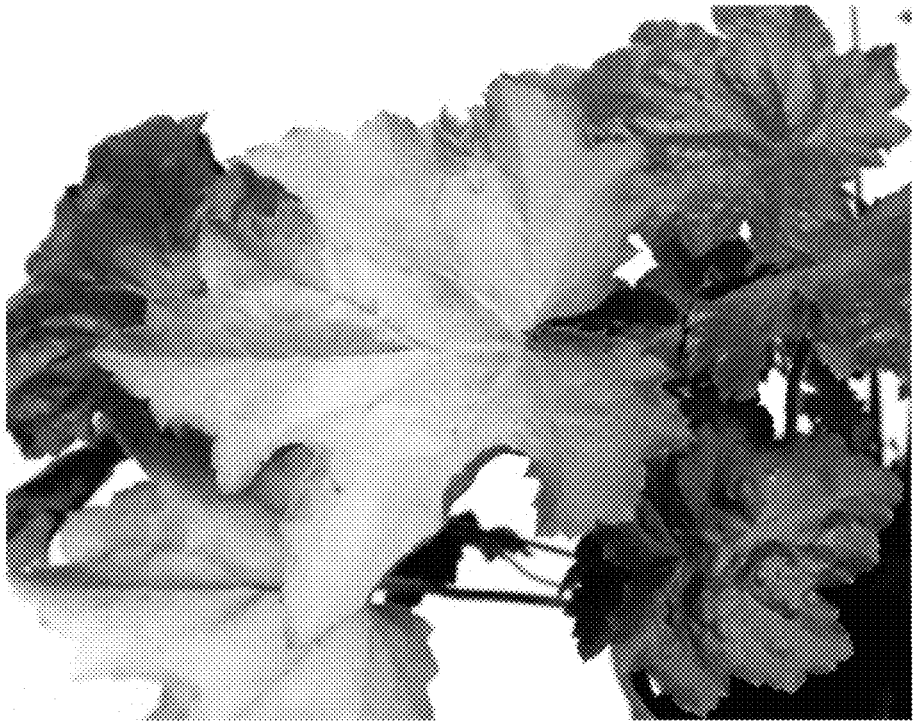

The photograph in FIG. 4 provides a close-up view of the mature foliage colors of 'MS2020'.

The colors in the photographs are as close as possible with the digital photography techniques available, the color values cited in the detailed botanical description accurately describe the colors of the new *Heuchera*.

DETAILED BOTANICAL DESCRIPTION OF THE PLANT

The following is a detailed description of 8 month-old plants of the new cultivar as grown outdoors in 17-cm containers in Boskoop, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—10 to 12 weeks, starting in mid-June in The Netherlands.

*Plant type.*—Herbaceous perennial.

*Plant habit.*—Broadly upright with inflorescences held above the foliage.

*Height and spread.*—An average of 25 cm in height (soil level to top of foliar plane), average of 42.8 cm in height (soil level to top of floral plane) and 47.5 cm in spread.

*Hardiness.*—At least in U.S.D.A. Zones 4 to 9.

*Diseases and pests.*—No susceptibility or resistance to diseases or pests has been observed.

*Root description.*—Fibrous roots on woody rootstalks, 158D in color.

*Propagation.*—Division and tissue culture.

*Root development.*—An average of 3 weeks for root initiation and 6 weeks to produce a rooted cutting.

*Growth rate.*—Moderate to highly vigorous.

*Branching habit.*—Flowering stems emerge from basal rosette, an average of 7 rosettes per plant, no lateral branches.

Foliage description:

*Leaf shape.*—Nearly orbicular in outline, slightly concave.

*Leaf division.*—Simple.

*Leaf base.*—Hastate, lobes free.

*Leaf apex.*—Short and abruptly acute.

*Leaf venation.*—Laciniate, upper surface 161B, lower surface 195A.

*Leaf margins.*—Crenate with short acute tips on each tooth, slightly to moderately coarsely undulate.

*Leaf attachment.*—Petiolate.

*Leaf arrangement.*—Alternate in basal rosettes.

*Leaf lobes.*—Lobed, an average of 5 lobes, shallow to medium in depth, divergent, lobe margins free.

*Leaf surface.*—Upper surface; moderately velvety, very slightly glossy, sparsely covered with very short strigose hairs 0.5 mm in length and closest to N155A in color, lower surface; slightly glossy, moderately covered with very short strigose hairs 1 mm in length and closest to N155A in color.

*Leaf color.*—Young upper surface; 175A, young lower surface; 187C, mature upper surface; a blend of 153D and 163C, changing late summer into fall 152A to 152B, mature lower surface; 182B.

*Leaf size.*—An average of 13.1 cm in length and 13.6 cm in width.

*Leaf quantity.*—An average of 8 per basal rosette.

*Petioles.*—An average of 19.2 cm in length and 3 mm in diameter, medium strength, both surfaces moderately glossy, color; upper surface 182B, lower surface 183D, tinged at distal end 195B, moderately covered with short soft hairs; an average of 1.5 mm in length, transparent to matching surface color.

*Stipules.*—Leafy stipule at the base of each leaf, average 1.7 cm in length, average 6 mm in width, acute tip, margins ciliate, 186A in color on both surfaces, surfaces glossy.

Flower description:

*Inflorescence type.*—Campanulate, numerous small bell-shaped flowers arranged on panicles on peduncles emerging from a basal rosette.

*Inflorescence size.*—An average of 23.5 cm in height and 5.7 cm in diameter.

*Inflorescence number.*—An average of 2.

*Flower fragrance.*—None.

*Flower quantity.*—Average of 150 flowers per flowering stem, 300 per plant.

*Flower lastingness.*—Average of one week.

*Flower buds.*—Elliptic in shape, an average of 3 mm in length and 2 mm in diameter, color; 154C, surface is matte and densely covered with very short glandular hairs; an average of 0.3 mm in length and too small to measure color.

*Flower aspect.*—Outward to slightly nodding.

*Flower type.*—Single, campanulate.

*Flower size*.—Average of 6.5 mm in height, 5 mm in diameter.

*Petals*.—Average of 5, rotate arrangement and implanted in the hypanthium at base, oblanceolate in shape, margin is entire, apex is acute, base is long acuminate, upper and lower surface is glabrous, smooth and matte, an average of 2 mm in length and 1 10 mm in width, color when opening and fully open upper and lower surface; NN155D.

*Calyx*.—Campanulate, sepals fused to hypanthium, 3 mm in length, 2.75 mm in diameter.

*Sepals*.—An average of 5, lower 66% fused into campanulate hypanthium, short oblong in shape, an average of 3 mm in length and 1.5 mm in width, margin is entire and fused into hypanthium, apex is obtuse, color; when opening and fully open upper surface 157D, tip and base 147D, when opening and fully open lower surface 145D, tip and lower half 152D, both surfaces are matte and densely covered with very short glandular hairs an average of 0.2 mm in length and too small to measure color.

*Peduncle*.—An average of 44.3 cm in length and 3 mm in diameter, color; 176A, primary flower aspect 50° to horizontal, secondary peduncle aspect to main peduncle 60°, moderate in strength, surface moderately glossy and densely covered with very short soft glandular hairs; average of 1 mm in length, 156D in color.

*Pedicels*.—An average of 3 mm in length and 0.5 mm in diameter, 176B in color, primary flower aspect straight on top of secondary pedicel, pedicels of secondary and tertiary flower aspect is 50° (0°=straight on top of primary peduncle), moderate in strength, surface is slightly glossy and moderately covered with very short soft glandular hairs an average of 0.2 mm in length and too small to measure color.

Reproductive organs:

*Gynoecium*.—Pistils; 2, 4 mm in length, stigma; club-shaped, 0.2 mm in diameter, style; an average of 3.75 mm in length and 145D in color, ovary; 145B in color.

*Androecium*.—Stamens; 5, anthers; ovate in shape, average of 0.5 mm in length and width, 23B in color, filament; 3 mm in length and NN155D in color, pollen; low in quantity, 22A in color.

*Seed/fruit*.—No fruit or seeds have been observed to date.

It is claimed:

1. A new and distinct cultivar of *Heuchera* plant named 'MS2020' as herein illustrated and described.

* * * * *